United States Patent
Vrckovnik et al.

(10) Patent No.: US 10,336,776 B1
(45) Date of Patent: Jul. 2, 2019

(54) INVERT EMULSIONS MADE WITH NON-PEG CONTAINING SILICONE BASED POLYHYDRIC EMULSIFIERS

(71) Applicants: Rick Vrckovnik, Toronto (CA); Fenbao David Zhang, Toronto (CA); Mark Riddle, Toronto (CA)

(72) Inventors: Rick Vrckovnik, Toronto (CA); Fenbao David Zhang, Toronto (CA); Mark Riddle, Toronto (CA)

(73) Assignee: SILTECH CORP, Toronto, ON (CA)

( * ) Notice: Subject to any disclaimer, the term of this patent is extended or adjusted under 35 U.S.C. 154(b) by 0 days.

(21) Appl. No.: 15/472,599

(22) Filed: Mar. 29, 2017

Related U.S. Application Data

(60) Provisional application No. 62/315,365, filed on Mar. 30, 2016.

(51) Int. Cl.
| | |
|---|---|
| *C07F 7/08* | (2006.01) |
| *A61K 8/58* | (2006.01) |
| *A61Q 19/00* | (2006.01) |
| *A61K 8/06* | (2006.01) |
| *A61Q 5/12* | (2006.01) |

(52) U.S. Cl.
CPC ............ *C07F 7/0838* (2013.01); *A61K 8/064* (2013.01); *A61K 8/585* (2013.01); *A61Q 5/12* (2013.01); *A61Q 19/00* (2013.01); *A61K 2800/30* (2013.01)

(58) Field of Classification Search
None
See application file for complete search history.

(56) References Cited

U.S. PATENT DOCUMENTS 7,279,503 B1 * 10/2007 O'Lenick, Jr. ...... B01F 17/0071
516/23

* cited by examiner

*Primary Examiner* — Clinton A Brooks
*Assistant Examiner* — Kofi Adzamli

(57) ABSTRACT

This patent relates to invert water in oil (w/o) and water in silicone (w/si) emulsions made using non PEG/PPG containing polyhydric silicone emulsifiers. The polyhydric silicone polymers are based on allyl trimethylolpropane and pentaerythritol modified organic groups and do not contain any PEG and/or PPG groups (also known as polyethylene glycol and polypropylene glycols, polyethers, polyglycols,). These emulsions show improved emulsification stability and provide a light feel compared to emulsions made with other silicone based PEG/PPG compounds which are commonly used in the field.

7 Claims, No Drawings

INVERT EMULSIONS MADE WITH NON-PEG CONTAINING SILICONE BASED POLYHYDRIC EMULSIFIERS

RELATED APPLICATIONS

This application claims priority to and benefit of U.S. Provisional Application No. 62/315,362 filed 30 Mar. 2016, the disclosure of which is incorporated herein for all purposes

FIELD OF THE INVENTION

This patent relates to invert water in oil (w/o) and water in silicone (w/si) emulsions made using non PEG/PPG containing polyhydric silicone emulsifiers. The polyhydric silicone polymers are based on allyl trimethylolpropane and pentaerythritol modified organic groups and do not contain any PEG and/or PPG groups (also known as polyethylene glycol and polypropylene glycols, polyethers, polyglycols,). These emulsions show improved emulsification stability and provide a light feel compared to emulsions made with other silicone based PEG/PPG compounds which are commonly used in the field.

BACKGROUND OF THE INVENTION

Silicone polyethers have long been used as slip additives, defoaming agents and many other industrial applications. They are used in personal care for use as conditioners, emollients and emulsifiers and invert emulsifiers and many other applications.

Many types of emulsifiers are available in the market that act as an invert emulsifier. Silicone based alkyl polyethers such as Silube J208-812 and J208-612, available from Siltech Corp in Toronto, have been used in this application. These silicone based alkyl polyethers act as low to medium HLB emulsifiers to make invert w/o emulsions. In addition they provide a good skin feel and water resistance. HLB is a measurement of the hydrophilic/hydrophobic balance in a surfactant and is normally based on PEG (polyglycol) compounds that have a large portion of organic and/or silicone moiety along with the PEG portion. Most invert emulsions use a surfactant with low to medium HLB.

U.S. Pat. No. 4,698,178 to Huttinger et al describes the use of silicone polyethers that have separate alkyl and polyether pendant groups for use as water in oil emulsifiers.

U.S. Pat. No. 6,133,370 to Gutek et al describes using Phenylpropyl based silicone polyethers as emulsifiers.

In each case, the silicone contains PEG groups. There is concern about dioxane and ethylene oxide levels contained in PEG compounds and also the genotoxicity of PEG based products. Because of safety concerns surrounding the use of PEG based products, there is a desire to make w/o and/or w/si emulsions using a silicone based invert emulsifier that does not contain any PEG groups.

U.S. Pat. No. 3,381,019 to Morehouse et al describes the use of a multi hydroxy silicone made by the reaction of a silicone hydride reacted with trimethylolpropane monoallylether. This patent describes applications in urethane foam and as defoamers, but not as w/o or w/si emulsifiers.

U.S. Pat. No. 5,916,992 to Wilt et al also describes the use of multi hydroxy silicone made by the reaction of a silicone hydride reacted with trimethylolpropane monoallylether for use in industrial coatings.

Silicones with propyl alcohol groups made from the reaction of silicone hydrides with allyl alcohol are known in the industry such as those provided by Siltech under the brand Silmer OH. These have been tested as invert emulsifiers, but the products do not have enough hydrophilicity to be useful as a w/o or w/si emulsifiers even in high concentrations of hydroxy groups.

SUMMARY OF THE INVENTION

The object of this invention is to provide w/o or w/si emulsions that are made using silicone based polyhydric emulsifiers which contain no PEG and/or PPG groups for use in personal care and other applications such as oil drilling muds and fluids and anywhere else where invert w/o and w/si emulsifiers are used.

There is also a desire in the industry to remove some PEG based products including silicone based PEG products in various personal care applications due to health concerns. We have surprisingly found that we can make stable w/o and w/si emulsions using silicone modified with allyl based trimethylol propane and/or pentaerythritol organic groups. These do not contain any PEG groups and despite having such a low to almost unmeasurable HLB, provide for stable invert emulsions with a light feel.

Water in oil emulsions are used in the personal care industry as they provide for smooth skin application and a nice feel. They are also milder than some o/w emulsions as they do not disturb the lipid bilayers in the skin. They are often used in sunscreens as it is well known in the industry that compared with the same percent of active sunscreen, using w/o emulsions are more efficient with higher SPF and have better water resistance than o/w emulsions.

The invert emulsions using these silicone based polyhydric compounds can be used for applications such as sunscreen, foundations, hand creams and any other invert w/o or w/si emulsions known in the industry. They provide an emulsion that has a light feel on the skin and breaks and wets out readily on the skin or hair for smooth application.

The w/o and w/si emulsions made using these innovative and versatile PEG-free invert emulsifiers have excellent uniformity and stability which can increase colour intensity in certain applications in personal care. They also provide uniform coverage for evenness of skin tone and enhanced sunscreen sensory performance when used in sunscreens. The emulsions have easier spreadability, and less whitening and tackiness compared to other standard invert emulsions. The invert emulsions made using these invert emulsifiers are also beneficial as they do not need co-emulsifiers or pigment dispersant additives which also help to reduce the complexity and costs. They also deliver good oil phase flexibility to meet increasing customer demand for improved sensory benefits, such as smooth texture, comfortable wear and low odor.

DETAILED DESCRIPTION OF INVENTION

This invention describes w/o and w/si invert emulsions made using silicone based polyhydric non PEG/PPG emulsifiers.

The structure of these emulsifiers is as follows:

$$CH_3-\underset{\underset{CH_3}{|}}{\overset{\overset{CH_3}{|}}{Si}}-(O-\underset{\underset{CH_3}{|}}{\overset{\overset{CH_3}{|}}{Si}})_x-(O-\underset{\underset{(CH_2)_o}{|}}{\overset{\overset{CH_3}{|}}{Si}})_y-(O-\underset{\underset{(CH_2)_{10}}{|}}{\overset{\overset{CH_3}{|}}{Si}})_z-\underset{\underset{CH_3}{|}}{\overset{\overset{CH_3}{|}}{Si}}-CH_3$$

with side chains: $CH_3$ on $(CH_2)_o$; and on $(CH_2)_{10}$ side: $C=O$, $O$, $CH_2-C(CH_2-OH)(CH_2-OH)-CH_2-G$ wherein;
x is an integer ranging from 1 to 100;
y is an integer ranging from 1 to 50;
z is an integer ranging from 1 to 50;
o is an integer ranging from 1 to 21;
G is selected from the group consisting of —$CH_3$; —OH and mixtures thereof.

The structure of these emulsifiers is as follows:

$$CH_3-\underset{\underset{CH_3}{|}}{\overset{\overset{CH_3}{|}}{Si}}-(O-\underset{\underset{CH_3}{|}}{\overset{\overset{CH_3}{|}}{Si}})_a-(O-\underset{\underset{(CH_2)_o}{|}}{\overset{\overset{CH_3}{|}}{Si}})_b-(O-\underset{\underset{(CH_2)_3}{|}}{\overset{\overset{CH_3}{|}}{Si}})_c-\underset{\underset{CH_3}{|}}{\overset{\overset{CH_3}{|}}{Si}}-CH_3$$

wherein;
a is an integer ranging from 1 to 100;
b is an integer ranging from 1 to 50;
c is an integer ranging from 1 to 50;
o is an integer ranging from 1 to 21;
G is selected from the group consisting of —$CH_3$—; —OH and mixtures thereof.

Preferred Embodiments

A silicone invert emulsifier having the following structure:

$$CH_3-\underset{\underset{CH_3}{|}}{\overset{\overset{CH_3}{|}}{Si}}-(O-\underset{\underset{CH_3}{|}}{\overset{\overset{CH_3}{|}}{Si}})_x-(O-\underset{\underset{(CH_2)_o}{|}}{\overset{\overset{CH_3}{|}}{Si}})_y-(O-\underset{\underset{(CH_2)_{10}}{|}}{\overset{\overset{CH_3}{|}}{Si}})_z-\underset{\underset{CH_3}{|}}{\overset{\overset{CH_3}{|}}{Si}}-CH_3$$

wherein;
x is 0;
y is 1;
z is 3;
o is 1;
G is —$CH_3$

A more preferred embodiment a silicone emulsifier having the following structure:

$$CH_3-\underset{\underset{CH_3}{|}}{\overset{\overset{CH_3}{|}}{Si}}-(O-\underset{\underset{CH_3}{|}}{\overset{\overset{CH_3}{|}}{Si}})_a-(O-\underset{\underset{(CH_2)_o}{|}}{\overset{\overset{CH_3}{|}}{Si}})_b-(O-\underset{\underset{(CH_2)_3}{|}}{\overset{\overset{CH_3}{|}}{Si}})_c-\underset{\underset{CH_3}{|}}{\overset{\overset{CH_3}{|}}{Si}}-CH_3$$

wherein;
a is 0;
b is 1;
c is 3;
o is 2;
G is —$CH_3$

Raw Materials

Silicone Hydride

Internal silicone hydrides are commercially available from a variety of sources including Siltech Corporation, Toronto, Ontario, Canada. They have the structure of:

$$-\overset{|}{\underset{|}{Si}}(O-\overset{|}{\underset{|}{Si}})_a(O-\overset{|}{\underset{H}{Si}})_b O-\overset{|}{\underset{|}{Si}}-$$

| Example | A | b | Molecular Weight (g/mol) |
|---|---|---|---|
| 1 | 2 | 1 | 370.5 |
| 2 | 150 | 3 | 11,619.4 |
| 3 | 0 | 4 | 404.0 |
| 4 | 8 | 4 | 996.8 |
| 5 | 24 | 8 | 2,583.6 |
| 6 | 20 | 10 | 2,407.4 |
| 7 | 100 | 10 | 8,335.4 |

Alpha-Olefin

Alpha-olefins are hydrocarbons with a primary double bond. They are available from a variety of sources including Chevron Chemicals they have the following structure:

$$CH_3(CH_2)_d CH=CH_2$$

| Example | d | Molecular Weight (g/mol) |
|---|---|---|
| 8 | 8 | 154.0 |
| 9 | 12 | 210.0 |
| 10 | 16 | 266.0 |
| 11 | 18 | 294.0 |
| 12 | 22 | 350.0 |
| 13 | 26 | 406.0 |

Example 14

Trimethylolpropane monoalkyl ether is commercially available from a variety of sources including Sigma Aldrich. It has the following structure.

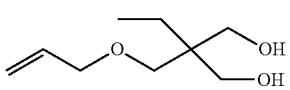

Example 15

Undecylenic trimethylolpropane is commercially available from a variety of sources including Sigma Aldrich. It has the following structure.

$CH_2=CH(CH_2)_8C(O)-R$ wherein:
R has the structure of:

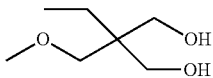

Silicone Emulsifier

Reaction of Silicone Hydride with Olefin and Allyl Trimethylolpropane

Silicone Hydride (examples 1-7) was placed into a reaction mixture, allyl trimethylol propane mono methyl ether (example 14) and alpha olefin (examples 8-13) were added into the reaction flask. Isopropyl alcohol (IPA) was added to the mixture and the temperature was increased from 25° C. to 80° C. Karstedt catalyst was added (0.05%) to the reaction mixture. The reaction mixture was allowed to run for 2 hours. After the reaction, the IPA was stripped off and the product was allowed to cool.

|  | Silicone Hydride | | Example 14 | Olefin | |
|---|---|---|---|---|---|
| Example | Example | Grams | Grams | Example | Grams |
| 16 | 2 | 192.03 | 2.88 | 8 | 5.09 |
| 17 | 2 | 188.61 | 4.24 | 11 | 7.16 |
| 18 | 2 | 184.36 | 2.76 | 13 | 12.88 |
| 19 | 3 | 66.89 | 28.81 | 9 | 104.30 |
| 20 | 3 | 62.93 | 54.21 | 10 | 82.87 |
| 21 | 3 | 77.69 | 33.46 | 8 | 88.85 |
| 22 | 4 | 101.26 | 17.68 | 10 | 81.06 |
| 23 | 4 | 120.62 | 42.11 | 8 | 37.27 |
| 24 | 4 | 89.77 | 15.67 | 12 | 94.56 |
| 25 | 5 | 107.30 | 7.23 | 11 | 85.47 |
| 26 | 5 | 110.42 | 29.75 | 12 | 59.83 |
| 27 | 5 | 122.40 | 57.70 | 9 | 19.90 |
| 28 | 6 | 113.57 | 73.88 | 10 | 12.55 |
| 29 | 6 | 101.42 | 36.65 | 11 | 61.93 |
| 30 | 6 | 84.01 | 6.07 | 12 | 109.92 |
| 31 | 7 | 137.06 | 2.86 | 13 | 60.08 |
| 32 | 7 | 167.12 | 17.44 | 8 | 15.44 |
| 33 | 7 | 164.87 | 30.97 | 9 | 4.15 |

Reaction of Silicone Hydride with Olefin and Mono Undecylenic Trimethylolpropane Silicone Hydride (examples 1-7) was placed into a reaction mixture, undecylenic trimethylolpropane (example 15) and alpha olefin (examples 8-13) were added into the reaction flask. Isopropyl alcohol (IPA) was added to the mixture and the temperature was increased from 25° C. to 80° C. Karstedt catalyst was added (0.05%) to the reaction mixture. The reaction mixture was allowed to run for 2 hours. After the reaction, the IPA was stripped off and the product was allowed to cool.

|  | Silicone Hydride | | Example 15 | Olefin | |
|---|---|---|---|---|---|
| Example | Example | Grams | Grams | Example | Grams |
| 34 | 2 | 190.06 | 4.91 | 8 | 5.04 |
| 35 | 2 | 185.76 | 7.19 | 11 | 7.05 |
| 36 | 2 | 182.53 | 4.71 | 13 | 12.76 |
| 37 | 3 | 60.57 | 44.98 | 9 | 94.45 |
| 38 | 3 | 52.60 | 78.13 | 10 | 69.27 |
| 39 | 3 | 69.30 | 51.46 | 8 | 79.25 |
| 40 | 4 | 95.17 | 28.64 | 10 | 76.19 |
| 41 | 4 | 104.66 | 63.00 | 8 | 32.34 |
| 42 | 4 | 84.95 | 25.57 | 12 | 89.48 |
| 43 | 5 | 104.57 | 12.14 | 11 | 83.29 |
| 44 | 5 | 99.68 | 46.30 | 12 | 54.02 |
| 45 | 5 | 101.25 | 82.29 | 9 | 16.46 |
| 46 | 6 | 89.60 | 100.50 | 10 | 9.90 |
| 47 | 6 | 89.54 | 55.79 | 11 | 54.67 |
| 48 | 6 | 82.20 | 10.24 | 12 | 107.56 |
| 49 | 7 | 135.65 | 4.88 | 13 | 59.47 |
| 50 | 7 | 157.19 | 28.29 | 8 | 14.52 |
| 51 | 7 | 148.25 | 48.02 | 9 | 3.73 |

Example 52

Silicone as Invert Emulsifier in Sunscreen

The following table shows the comparison of using these new non-PEG containing silicone emulsifiers vs a standard PEG containing silicone emulsifier.

| Part ID | Ingredients | Wt % | Wt % | Wt % | Wt % | Wt % |
|---|---|---|---|---|---|---|
| A | D.I. Water | 54.30 | 54.30 | 54.30 | 54.3 | 54.3 |
|  | Propylene Glycol | 5.0 | 5.0 | 5.0 | 5.0 | 5.0 |
|  | NaCl | 1.0 | 1.0 | 1.0 | 1.0 | 1.0 |
|  | Na₂EDTA | 0.10 | 0.10 | 0.10 | 0.1 | 0.1 |
|  | Standard PEG Emulsifier | 5.00 | 0 | 0 | 0 | 0 |
|  | Example 16 | 0 | 5.00 | 0 | 0 | 0 |
|  | Example 31 | 0 | 0 | 5.00 | 0 | 0 |
|  | Example 34 | 0 | 0 | 0 | 5.00 | 0 |
|  | Example 39 | 0 | 0 | 0 | 0 | 5.00 |
|  | Silwax D02 | 2.0 | 2.0 | 2.0 | 2.0 | 2.0 |

-continued

| Part ID | Ingredients | Wt % | Wt % | Wt % | Wt % | Wt % |
|---|---|---|---|---|---|---|
| | Caprylic/capric Triglyceride | 3.50 | 3.50 | 3.50 | 3.50 | 3.50 |
| | Isopropyl Myristate | 8.00 | 8.00 | 8.00 | 8.00 | 8.00 |
| | Coconut Oil | 1.00 | 1.00 | 1.00 | 1.00 | 1.00 |
| | Raspberry Seed Oil | 1.00 | 1.00 | 1.00 | 1.00 | 1.00 |
| | C10-30 Alkyl Acrylate | 2.50 | 2.50 | 2.50 | 2.50 | 2.50 |
| | Titanium Dioxide | 2.00 | 2.00 | 2.00 | 2.00 | 2.00 |
| | Octyl Methoxycinnamate | 7.00 | 7.00 | 7.00 | 7.00 | 7.00 |
| | Benzophenone-3 | 5.00 | 5.00 | 5.00 | 5.00 | 5.00 |
| | Avobenzone | 2.00 | 2.00 | 2.00 | 2.00 | 2.00 |
| | Phenonip | 0.60 | 0.60 | 0.60 | 0.60 | 0.60 |
| C | Sharomix MCI | q.s. | q.s. | q.s. | q.s. | q.s. |
| | Fragrance | q.s. | q.s. | q.s. | q.s. | q.s. |
| | Total | 100% | 100% | 100% | 100% | 100% |

Procedure:

1. Combine ingredients in Part B and heat up to 70° C., blend well using Bamix mixer until homogeneous, then heat up to 75~80° C.
2. Combine Part A and mix well and then heat up to 75~80° C.
3. Add Part A into Part B slowly under mixing. Keep mixing for 5 minutes after finishing the addition, then cool down to 45° C. and apply high shear for 1 minute at 20,000 rpm.
4. Add Part C into batch and mix well.

Example 52

W/O Make-Up Formulation Comparing New Non-PEG Containing Emulsifier

The following table shows the comparison of using these new non-PEG containing silicone emulsifiers vs a standard PEG containing silicone emulsifier (Silube J208-812 from Siltech)

| Part ID | Ingredients | Wt % | Wt % | Wt % | Wt % | Wt % |
|---|---|---|---|---|---|---|
| A | D.I. Water | 49.51 | 49.51 | 49.51 | 49.51 | 49.51 |
| | Propylene Glycol | 5.0 | 5.0 | 5.0 | 5.0 | 5.0 |
| | NaCl | 1.0 | 1.0 | 1.0 | 1.0 | 1.0 |
| B | Standard PEG Emulsifier | 5.00 | 0 | 0 | 0.0 | 0.0 |
| | Example 16 | 0 | 5.00 | 0 | 0.0 | 0.0 |
| | Example 31 | 0 | 0 | 5.00 | 0.0 | 0.0 |
| | Example 34 | 0 | 0 | 0.0 | 5.00 | 0.0 |
| | Example 39 | 0 | 0 | 0.0 | 0.0 | 5.00 |
| | Silwax D02 | 2.0 | 2.0 | 2.0 | 2.0 | 2.0 |
| | Caprylic/capric Triglyceride | 10.00 | 10.00 | 10.00 | 10.00 | 10.00 |
| | Isopropyl Myristate | 8.00 | 8.00 | 8.00 | 8.00 | 8.00 |
| | Siltech F100 | 1.00 | 1.00 | 1.00 | 1.00 | 1.00 |
| | Argan Oil | 6.00 | 6.00 | 6.00 | 6.00 | 6.00 |
| | C10-30 Alkyl Acrylate | 1.50 | 1.50 | 1.50 | 1.50 | 1.50 |
| | Unipure LC 987 AS | 3.68 | 3.68 | 3.68 | 3.68 | 3.68 |
| | IRIS91-Y-77492 | 0.74 | 0.74 | 0.74 | 0.74 | 0.74 |
| | IRIS91-R-77491 | 0.22 | 0.22 | 0.22 | 0.22 | 0.22 |
| | IRIS91-B-77499 | 0.07 | 0.07 | 0.07 | 0.07 | 0.07 |
| | Phenonip | 0.60 | 0.60 | 0.60 | 0.60 | 0.60 |
| C | Sharomix MCI | q.s. | q.s. | q.s. | q.s. | q.s. |
| | Fragrance | q.s. | q.s. | q.s. | q.s. | q.s. |
| | Total | 100% | 100% | 100% | 100% | 100% |

Procedure:

1. Combine ingredients in Part B and blend well using Bamix mixer until homogeneous, then heat up to 75~80° C.
2. Combine Part A and mix well and then heat up to 75~80° C.
3. Add Part A into Part B slowly under mixing. Keep mixing for 5 minutes after finishing the addition and then cool down to 45° C. and apply high shear for 1 minute at 2,000 rpm.
4. Add Part C into batch and mix well.

Example 53

W/Si Emulsion Formulation Using Silicone

The following table shows the comparison of using these new non-PEG containing silicone emulsifiers vs a standard PEG containing silicone emulsifier.

| Part ID | Ingredients | Wt % | Wt % | Wt % | Wt % | Wt % |
|---|---|---|---|---|---|---|
| A | D.I. Water | 77.2 | 76.2 | 76.2 | 76.2 | 76.2 |
| | Propylene Glycol | 5.0 | 5.0 | 5.0 | 5.0 | 5.0 |
| | $MgSO_4 \cdot 7H_2O$ | 2.0 | 2.0 | 2.0 | 2.0 | 2.0 |
| B1 | Standard PEG Emulsifier | 1.60 | 0 | 0 | 0 | 0 |
| | Example 16 | 0 | 1.60 | 0 | 0 | 0 |
| | Example 31 | 0 | 0 | 1.60 | 0 | 0 |
| | Example 34 | 0 | 0 | 0 | 1.60 | 0 |
| | Example 39 | 0 | 0 | 0 | 0 | 1.60 |
| | Silwax D02 | 1.0 | 1.0 | 1.0 | 1.0 | 1.0 |
| | Siltech F-100 | 8.7 | 8.7 | 8.7 | 8.7 | 8.7 |
| | D5 | 4.0 | 4.0 | 4.0 | 4.0 | 4.0 |
| B2 | Magnesium Stearate | 0.3 | 0.3 | 0.3 | 0.3 | 0.3 |
| C | Sharomix MCI | 0.2 | 0.2 | 0.2 | 0.2 | 0.2 |
| | Total | 100% | 100% | 100% | 100% | 100% |

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth hereinabove but rather that the claims be construed as encompassing all the features of patentable novelty which reside in the present invention, including all features which would be treated as equivalents thereof by those skilled in the art to which the invention pertains.

The invention claimed is:

1. A silicone emulsifier having the following structure:

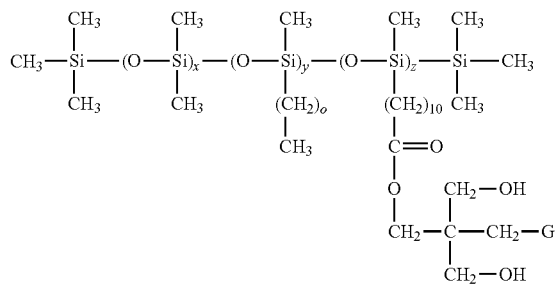

wherein;
x is an integer ranging from 1 to 100;
y is an integer ranging from 1 to 50;
z is an integer ranging from 1 to 50;
o is an integer ranging from 1 to 21;
G is selected from the group consisting of $CH_3$; OH and mixtures thereof.

2. A silicone emulsifier of claim 1 wherein o is 11.

3. A silicone emulsifier having the following structure:

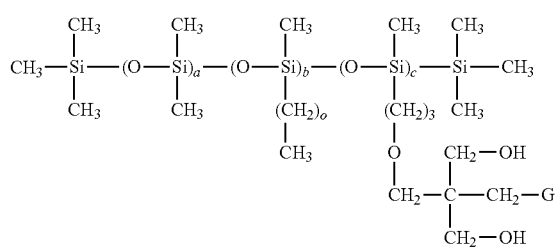

wherein;
a is an integer ranging from 1 to 100;
b is an integer ranging from 1 to 50;
c is an integer ranging from 1 to 50;
o is an integer ranging from 1 to 21;
G is selected from the group consisting of $CH_3$; OH; and mixtures thereof.

4. A silicone emulsifier of claim 3 having the following structure;

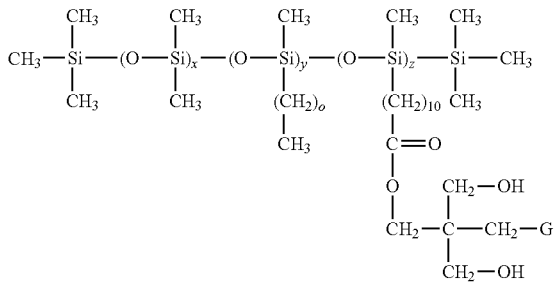

wherein;
x is 0;
y is 1;
z is 3;
o is 1;
G is $CH_3$.

5. A silicone emulsifier of claim 4 wherein o is 11.

6. A silicone emulsifier of claim 3 having the following structure;

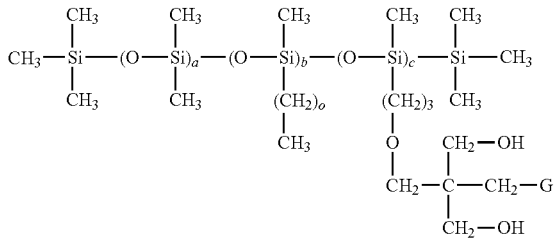

wherein;
a is 0;
b is 1;
c is 3;
o is 2;
G is $CH_3$.

7. A silicone emulsifier of claim 3 wherein o is 11.

* * * * *